(12) United States Patent
Kanesaka

(10) Patent No.: US 6,277,133 B1
(45) Date of Patent: Aug. 21, 2001

(54) CONNECTOR FOR SMALL CONDUITS

(76) Inventor: Nozomu Kanesaka, 81 Greenwoods Rd., Old Tappan, NJ (US) 07675

( * ) Notice: Subject to any disclaimer, the term of this patent is extended or adjusted under 35 U.S.C. 154(b) by 0 days.

(21) Appl. No.: 09/527,821

(22) Filed: Mar. 17, 2000

(51) Int. Cl.⁷ .................................................. A61B 17/04
(52) U.S. Cl. ............................................................ 606/153
(58) Field of Search ..................................... 606/151–154

(56) References Cited

U.S. PATENT DOCUMENTS

| | | | |
|---|---|---|---|
| 4,470,415 | * | 9/1984 | Wozoniak ............................. 606/153 |
| 5,139,505 | * | 8/1992 | Palmieri ............................... 606/154 |
| 5,254,127 | * | 10/1993 | Wholey et al. ...................... 606/153 |
| 5,916,226 | * | 6/1999 | Tozzi ................................... 606/153 |
| 5,997,573 | * | 6/1999 | Quijano et al. ........................ 623/1 |
| 6,036,704 | * | 3/2000 | Yoon .................................... 606/153 |

FOREIGN PATENT DOCUMENTS

0701417 * 12/1994 (EP) .............................. A61B/17/10

* cited by examiner

*Primary Examiner*—Gary Jackson
(74) *Attorney, Agent, or Firm*—Kanesaka & Takeuchi

(57) ABSTRACT

A connector of the invention is used to easily connect small conduits, such as blood vessel. The connector is formed of an elongated hollow support member to be located inside the small conduits, and a holding device disposed outside the support member for holding the small conduits together with the support member. The holding device includes cylindrical portions, which are disposed outside the support member and shrinkable when a radially inward force is applied, and a plurality of connecting portions situated between the cylindrical portions and extending radially outwardly from the cylindrical portions. The connecting portions are bent and disposed over one of the cylindrical portions when the holding device holds the small conduits at the cylindrical portions.

7 Claims, 1 Drawing Sheet

CONNECTOR FOR SMALL CONDUITS

BACKGROUND OF THE INVENTION AND RELATED ART STATEMENT

The present invention relates to a connector for small conduits for easily connecting two small conduits together. In particular, the connector is suitable for connecting small blood vessels.

In a surgery, blood vessels and conduits are often cut in treating or removing a diseased portion of a patient. In this case, after the necessary treatment has been completed, the blood vessels and conduits are connected as they were before or to other blood vessels and conduits. Also, the blood vessels and conduits may have diseases by themselves, such as weakened blood vessel wall, clogging, tumor and so on. In this case, the blood vessel and conduit including the diseased portion is cut to remove the diseased portion, and the healthy portions of the blood vessel and conduit are connected together.

In case the blood vessel and conduit are connected to other blood vessel and conduit in a surgery, the blood vessels and conduits are sewed together even if the blood vessels and conduits are small. Sewing the small blood vessels and conduits is very troublesome and time consuming. However, there is no other method in connecting the two small conduits together.

The present invention has been made in view of the trouble in connecting two small conduits including the blood vessel in a surgery, and an object of the invention is to provide a connector for connecting two small conduits easily in a short period of time.

Another object of the invention is to provide a connector for small conduits as stated above, wherein the connector can securely connect the small conduits without looseness for a long period of time.

A further object of the invention is to provide a connector for small conduits as stated above, wherein the connector can help connecting the conduits naturally.

A still further object of the invention is to provide a connector for small conduits as stated above, wherein the connector can be manufactured easily at a low cost.

Further objects and advantages of the invention will be apparent from the following description of the invention.

SUMMARY OF THE INVENTION

A connector of the invention is designed to connect two small conduits, such as blood vessels, in an operation or surgery. The connector is formed of an elongated hollow support member to be located inside the small conduits, and a holding device disposed outside the support member for holding the small conduits together with the support member.

The holding device includes cylindrical portions, preferably two cylindrical portions, and a plurality of connecting portions situated between the cylindrical portions. The cylindrical portions are shrinkable when a radially inward force is applied. The connecting portions extend radially outwardly from the cylindrical portions, and can be bent to be disposed on the cylindrical portions. The support member is relatively rigid. Thus, even if a radially inward force is applied to the support member, the support member is not substantially deformed or collapsed.

In use, the holding device is slidably disposed over one of the small conduits to be connected, and the support member is inserted into the small conduits to bridge the small conduits. Then, the cylindrical portions are moved to be located above the support member with the small conduits therebetween. Then, the cylindrical portions are pushed radially inwardly to hold the small conduit between the cylindrical portion and the support portion. Thereafter, the cylindrical portions are moved to contact each other to thereby allow the ends of the small conduits to contact with each other. Then, the connecting portions are bent and disposed over one of the cylindrical portions to lock the connecting portions. Preferably, the connecting portions are disposed on both cylindrical portions.

In the invention, the relatively large and shrinkable cylindrical portions are disposed over the small conduits, and the rigid support member is disposed inside the small conduits. Thus, the support member and the holding device can be easily arranged over the small conduits to be connected. Also, when the cylindrical portions are pushed, the small conduits can be held surely between the cylindrical portions and the support member.

In the invention, the connecting portions are formed between the cylindrical portions to allow the cylindrical portions to contact with each other. When the cylindrical portions are contacted by squeezing the connecting portions, the end portions of the small conduits or blood vessels are contacted with each other, as well. Since the end portions of the blood vessels contact with each other, the end portions can be naturally cured or connected in the future. Thus, the connector can help curing the blood vessels naturally.

Also, in the invention, the connecting portions are bent over the cylindrical portions. Thus, the cylindrical portions moved close to each other are not separated. In case the connecting portions are bent onto two cylindrical portions, i.e. in opposite directions, the cylindrical portions are surely connected together by the connecting portions.

Preferably, each cylindrical portion includes a plurality of first elongated members arranged side by side to form a cylindrical net. At least a part of the respective first elongated members is bent when the radially inward force is applied, so that the diameter of the cylindrical portion can be reduced. The support member is formed of a plurality of second elongated members connected to each other to form a cylindrical net. The second elongated members do not substantially bend when the radially inward force is applied.

Preferably, each connecting portion is formed of two legs connected to the cylindrical portions, respectively, and a pre-bent portion situated between the two legs. When the holding device is prepared, portions of the legs connected to the cylindrical portions are situated away from each other. However, when the connecting portions are disposed over the cylindrical portions, the separated portions are squeezed so that the legs are closely contacted to each other. In this procedure, as explained before, the end surfaces of the blood vessels held between the support member and the cylindrical portions are contacted.

In the invention, the cylindrical portions may have a plurality of projections at the inner surfaces thereof to grip the small conduits or blood vessels.

DETAILED DESCRIPTION OF PREFERRED EMBODIMENTS

Embodiments of the connector of the invention will be explained with reference to the accompanying drawings.

The connector of the invention is designed to connect small conduits, such as blood vessels, in an operation or surgery. Generally, the connector connects two blood vessels having a diameter of 2.5–6 mm cut in an operation, and is left in a body of a patient. The connector helps curing or naturally connecting the blood vessels. Incidentally, the conduits with the diameter more than 6 mm may be connected by the connector of the invention, but such conduits may be easily connected together by sewing without using the connector of the invention.

Figure 1:
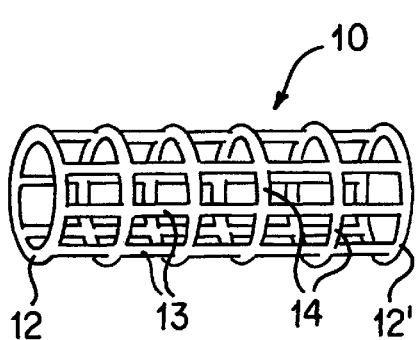
FIG. 1 is an explanatory perspective view of a support member of the connector of the invention.
Figure 2:
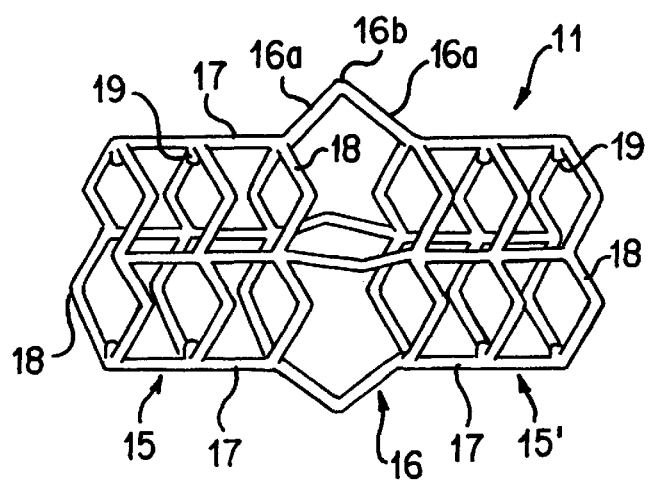
FIG. 2 is an explanatory perspective view of a holding device of the connector of the invention.

The connector is formed of a support member 10, as shown in FIG. 1, and a holding member 11, as shown in FIG. 2. The support member 10 has a cylindrical shape, and is formed of circular end portions 12, 12', a plurality of lateral members 13 situated parallel to each other between the end portions 12, 12', and circular middle portions 14 situated between the end portions 12, 12'. The end portions 12, 12', lateral members 13 and middle portions 14 are connected together to form a net shape.

The end portions 12, 12', lateral members 13 and middle portions 14 may be individually formed by wires and fixed together, but these portions and members may be integrally formed of a cylindrical metal member by etching or laser cutting. The support member 10 may be made of resin.

It is required in the invention that the support member 10 has a net shape or small holes therein not to provide adverse affect to the cells of the blood vessel, and is not deformable in the radial directions when the radial force is applied. Thus, the end portions 12, 12', lateral members 13 and middle portions 14 need not have the shapes as explained above, and may have any shapes as long as the above requirements are satisfied.

The holding member 11 as shown in FIG. 2 is formed of two cylindrical portions 15, 15', and connecting members 16 for connecting the cylindrical portions 15, 15'. Each cylindrical portion 15 or 15' has elongated portions 17 situated parallel to each other and arranged in a circular form, and peripheral portions 18 in a circular form when viewed from a left or right side in FIG. 2. The peripheral portion 18 is partially bent between two elongated portions 17 in a longitudinal direction from the left to right side in FIG. 2. Projections 19 project inwardly from the peripheral portions 18. Since the peripheral portions 18 are partially bent, when a radially inward force is applied to the cylindrical portions 15, 15', the diameters of the cylindrical portions 15, 15 can be reduced easily.

The connecting member 16 is formed of two legs 16a bent in a middle or bent portion 16b, and projects radially outwardly from the cylindrical portions 15, 15'. The connecting members 16 connect the elongated members 17 between the cylindrical portions 15, 15'. When the holding member 11 is formed, the legs are 16a slightly spaced from each other, e.g. 1–3 mm, at the bottoms connected to the elongated portions 17.

The elongated members 17 with the connecting members 16, and to the peripheral portions 18 may be separately formed by wires and fixed together, but these portions and members may be integrally formed of a cylindrical metal member by etching or laser cutting. After the cylindrical portions 15, 15' with the connecting members 16 in the linear shape are formed, the connecting members 16 are bent to form the bent portion 16b.

It is required in the invention that the cylindrical portions 15, 15' have a net shape or small holes therein to prevent adverse affect to the cells of the blood vessel, and is deformable in the radial directions when the radial force is applied. Thus, the cylindrical portions 15, 15' need not have the shapes as explained above, and may have any shape as long as the above requirements are satisfied.

The diameter of the cylindrical portions 15, 15' is greater than that of the support member 10 when the holding member 11 is formed. It is preferable to prepare several support members 10 with different sizes according to the size of the conduits to be connected. However, since the holding member 11 is formed collapsible over the support member 10, the holding member 11 may be one size applicable to all the different sizes of the support members 10.

When the connector of the invention is used, the holding member 11 is disposed over one of the two conduits C, C' or blood vessels. Then, the support member 10 is inserted into the conduits or blood vessels to bridge or connect the two end portions of the blood vessels. At this point, the end surfaces of the blood vessels may be slightly spaced apart from each other.

Figure 3:
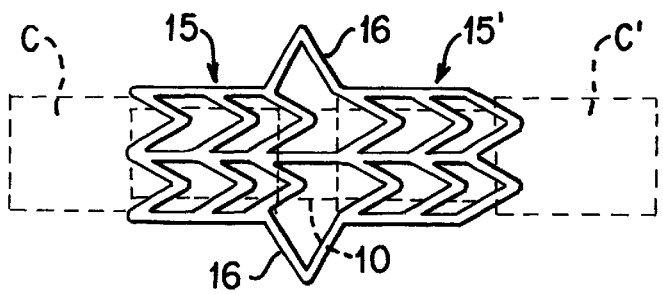
FIGS. 3–5 are explanatory side views of the connector for showing the procedures of connecting small conduits.

Then, the holding member 11 is moved to be disposed over the two end portions of the blood vessels C, C' with the support member 10 therein. Thereafter, the cylindrical portions 15, 15' are pushed to reduce the diameter, as shown in FIG. 3, so that the blood vessels C, C' are held between the cylindrical portions 15, 15' and the support member 10.

Figure 4:
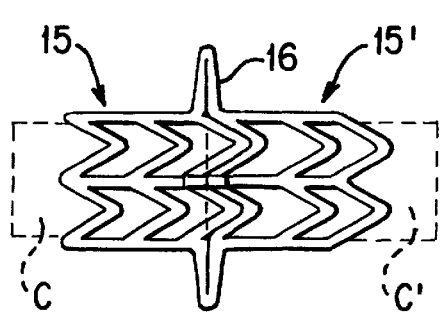
Figure 5:
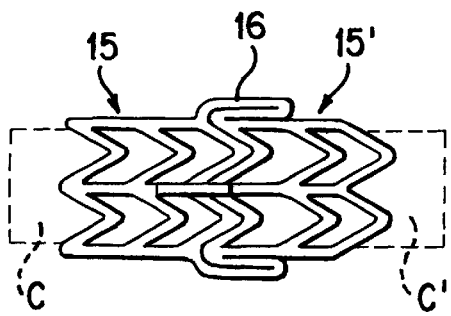

Then, the legs 16a of the connecting members 16 are pushed or squeezed to contact each other, so that the blood vessels C, C' are moved over the support member 10 or slightly pulled while being held on the support member 10 to allow the end surfaces of the blood vessels C, C' to contact each other. This condition is shown in FIG. 4.

Since the end surfaces of the blood vessels C, C' are forcibly contacted with each other in the above step, the end surfaces are naturally cured or connected after the mechanical connection by the connector of the invention. Thus, the connector of the invention is very useful.

Finally, the legs 16a of the connecting members 16 are bent over the cylindrical portions 15, 15'. In this example, two connecting portions 16 are bent over the cylindrical portion 15', while the connecting portions between the two bent over the cylindrical portion 15' are bent over the cylindrical portion 15. Thus, the cylindrical portions 15, 15' are surely locked or connected by the connecting portions 16. The connecting members 16 may be bent in the circumferential direction.

In the connector of the invention, the small conduits or blood vessels can be easily and securely connected together while the natural curing is being promoted. The connector is very useful in the surgery.

While the invention has been explained with reference to the specific embodiments of the invention, the explanation is illustrative, and the invention is limited only by the appended claims.

What is claimed is:

1. A connector for connecting small conduits, comprising:
   an elongated hollow support member adapted to be located inside the small conduits so that end portions of the small conduits are disposed over the support member, and
   a holding device disposed outside the support member for holding the small conduits together with the support member, said holding device including cylindrical portions to be disposed outside the support member and being shrinkable when a radially inward force is applied, and a plurality of connecting portions situated between the cylindrical portions and extending radially outwardly from the cylindrical portions, said connecting portions being bent and disposed over at least one of the cylindrical portions when the holding device holds the small conduits between the cylindrical portions and the support member.

2. A connector according to claim 1, wherein each cylindrical portion includes a plurality of first elongated members to form a cylindrical net, at least a part of the first elongated members being bent when the radially inward force is applied.

3. A connector according to claim 2, wherein said support member includes a plurality of second elongated members to form a cylindrical net, said second elongated members being arranged so that the second elongated members do not substantially bend when the radially inward force is applied.

4. A connector according to claim 2, wherein each connecting portion is formed of two legs connected to the cylindrical portions, and a pre-bent portion situated between the two legs.

5. A connector according to claim 4, wherein portions of the legs connected to the cylindrical portions in each connecting portion are situated away from each other when the holding device is prepared, said legs being closely contacted to each other when the connecting portion is disposed over at least one of the cylindrical portions.

6. A connector according to claim 5, wherein one of the connecting portions is disposed over one of the cylindrical portions, and another of the connecting portions is disposed over the other of the cylindrical portions to prevent separation of the cylindrical portions.

7. A connector according to claim 1, wherein said cylindrical portions have a plurality of projections at inner surfaces thereof to grip the small conduits.

* * * * *